United States Patent
Potas et al.

(10) Patent No.: US 12,222,341 B2
(45) Date of Patent: Feb. 11, 2025

(54) GAS MONITOR AND METHOD OF DETECTING GAS, INCLUDING A RIPENING MONITOR

(71) Applicant: POST HARVEST IP PTY LTD, Pyrmont (AU)

(72) Inventors: Michael Potas, St. Peters (AU); Gennadiy Volkov, St. Peters (AU); Alexander Hatzimihali, St. Peters (AU); Joshua Dunford, St. Peters (AU); Jonathan Shannon, Pyrmont (AU); Alex Matthews, St. Peters (AU); Jason Robert Potas, St. Peters (AU)

(73) Assignee: POST HARVEST IP PTY LTD, New South Wales (AU)

( * ) Notice: Subject to any disclaimer, the term of this patent is extended or adjusted under 35 U.S.C. 154(b) by 67 days.

(21) Appl. No.: 17/760,377

(22) PCT Filed: Feb. 10, 2021

(86) PCT No.: PCT/AU2021/050115
§ 371 (c)(1),
(2) Date: Aug. 9, 2022

(87) PCT Pub. No.: WO2021/159180
PCT Pub. Date: Aug. 19, 2021

(65) Prior Publication Data
US 2023/0228723 A1    Jul. 20, 2023

(30) Foreign Application Priority Data
Feb. 10, 2020    (AU) ................ 2020900352

(51) Int. Cl.
*G01N 33/00*    (2006.01)
*G01N 1/40*    (2006.01)

(52) U.S. Cl.
CPC ......... *G01N 33/0014* (2013.01); *G01N 1/405* (2013.01); *G01N 33/0019* (2024.05)

(58) Field of Classification Search
None
See application file for complete search history.

(56) References Cited

U.S. PATENT DOCUMENTS 3,366,456 A * 1/1968 Andreatch ............. G01N 30/68
436/154
3,650,090 A * 3/1972 Temple .................. G01N 1/405
95/82

(Continued)

FOREIGN PATENT DOCUMENTS

DE    3928102 A1 *    2/1991    ............ G01N 1/405
JP    H07248324 A *    3/1994

OTHER PUBLICATIONS

Janssen, S. et al., "Ethylene Detection in Fruit Supply Chains", Philosophical Transactions of the Royal Society, 2014, pp. 1-21.*

(Continued)

*Primary Examiner* — Daniel S Larkin
(74) *Attorney, Agent, or Firm* — Christopher A. Proskey; BrownWinick Law Firm

(57) ABSTRACT

A gas monitor configured to monitor at least one target gas in an environmental mixture, by separating and concentrating the target gas and then adjusting for the concentration factor. The adjustment may also take into account sensor sensitivities to other gases. Methods for adjustment of target gas results are described.

18 Claims, 15 Drawing Sheets

(56) References Cited

U.S. PATENT DOCUMENTS

| | | | | |
|---|---|---|---|---|
| 3,762,878 | A * | 10/1973 | Villalobos | G01N 30/68 |
| | | | | 436/154 |
| 10,509,007 | B1 * | 12/2019 | Henshaw | G01N 1/18 |
| 2002/0192117 | A1 | 12/2002 | Lewis | |
| 2004/0210099 | A1 * | 10/2004 | Shiratori | A23L 3/3445 |
| | | | | 73/24.06 |
| 2007/0077176 | A1 | 4/2007 | Lambert et al. | |
| 2012/0216597 | A1 | 8/2012 | Park et al. | |
| 2014/0291170 | A1 * | 10/2014 | Goecks | G01N 27/4045 |
| | | | | 204/402 |
| 2016/0139088 | A1 | 5/2016 | Ovadia et al. | |
| 2017/0219543 | A1 | 8/2017 | Lowy | |
| 2021/0172913 | A1 * | 6/2021 | Wang | G01N 1/405 |

OTHER PUBLICATIONS

Sklorz, A. et al., "Approaches to Increase the Sensitivity of Miniaturized Ethylene Concentration Measurement Systems in the Fresh Fruit Chain" Aug. 26, 2016.
International Search Report and Written Opinion—PCT/AU2021/050115—May 11, 2021.

* cited by examiner

GAS MONITOR AND METHOD OF DETECTING GAS, INCLUDING A RIPENING MONITOR

TECHNICAL FIELD

The present technology relates generally to gas monitors and methods of detecting gas in certain atmospheres. One application of the technology is in produce-ripening monitors, and methods for monitoring gases that issue from produce as it ripens. Applications of the monitors and methods are in estimating and/or predicting the ripeness of produce.

The technology relates generally also to systems and methods of monitoring the presence of one or more selected aerosolized or gaseous compounds, which may be present in any selected atmosphere, such as toilets, offices, bedrooms, dwellings, hotels, containers, machinery sheds and the like.

The monitors and methods are particularly suited for monitoring aerosolized or gaseous ethylene but there may be other gases which are suitable to be monitored, including oxygen, carbon dioxide, carbon monoxide, or types of volatile organic compound (VOC).

BACKGROUND

It is often useful to be able to understand the composition of gas mixtures, such as air. The air in certain closed atmospheres, such as buildings, office blocks, toilet cubicles, can also change, and it can be useful to understand the changing composition of those closed atmospheres. One economically important closed atmosphere is that inside a shipping container which includes ripening produce. The shipping container can be refrigerated.

Certain aerosolized or gaseous compounds issue from ripening produce. Reaching a threshold level, or changing amounts of one or more of the compounds provides an indicator of different stages of the ripening process, or can provide indicators of certain anomalies in the ripening process.

For various reasons there are technical difficulties in accurately monitoring the issued aerosolized or gaseous compounds.

First, the amounts of certain gaseous compounds released from the fruit as it ripens can be very small, but can have a large impact on the fruit in the container. In those environments, the concentrations of certain important aerosolized or gaseous compounds when the produce is ripening are so small that the sensors for sensing the compounds cannot easily detect any change above background levels.

Additionally, available ripening gas measurement sensors are known to exhibit drift to sensor reading values such that gas values become erroneous, or such that external calibration means are required, which results in unreliability readings and the ability to properly predict produce ripening levels.

It also known that gas sensors suitable for reading very low concentrations of gasses, such as in the parts per billion range, may be unintentionally overloaded with high gas concentrations, which can damage the sensor or add errors to gas sensor readings.

Also, various sensors have sensitivities to other gases which also are associated with ripening produce. The presence of one gas or aerosolized compound can interfere with the sensing of another gas or aerosolized compound.

The present invention seeks to ameliorate one or more of the abovementioned disadvantages and/or seeks to provide a new alternative.

SUMMARY

Broadly there is provided in the present technology a method of assessing the concentration of a target gas component in an environment, the method including the steps of increasing the concentration of the target gas component in an environmental sample by separating the target gas from the sample into a storage zone and then detecting the amount of the target gas in the storage zone and correcting the result for the increased concentration.

Broadly, the present technology also provides a produce ripening monitor for monitoring at least one target gas by taking measurements of the target gas, and other gases to which target gas sensors are sensitive, and correcting the target gas result on the basis of the other gas levels.

Broadly the present technology provides a ripening monitor which includes a conditioner which is configured to produce a controlled atmosphere. The advantage of the controlled atmosphere is to provide known conditions of humidity and/or temperature and pressure in a target gas concentrator.

In accordance with one aspect of the present technology, there is provided a method of measuring the concentration of a target gaseous or aerosolized compound in a gaseous environment, the method including the steps of:
  extracting a selected sample quantity of the gaseous environment into a target gas measurement system;
  separating the target gas or aerosolized compound from the quantity of sample gas, into a store;
  sensing, with a target gas sensor, the amount or concentration of the target gaseous or aerosolized compound in the store;
  receiving in a processor, data from the target gas sensor relating to the amount or concentration of the target gaseous or aerosolized compound;
  converting, in a processor, the target gas sensor data, with a conversion algorithm, to obtain environmental concentration data of the target gaseous or aerosolized compound; and
  storing in a data store or displaying on a display, the environmental concentration data, or transmitting the environmental concentration data to a remote server or processor.

In one embodiment, the method further includes the step of measuring with a sample gas sensor the quantity of the gas sample in the gas measurement system.

In one embodiment, the method further includes the step of receiving, into a processor, data relating to the selected quantity of sample gas.

In one embodiment, the method further includes a step wherein the algorithm takes into account data from the sample gas sensor relating to the sample gas quantity and/or one or more physical qualities taken from the group consisting of: temperature, volume, pressure, and humidity.

In one embodiment, the method further includes a step wherein the amount or concentration of the target gas is calculated by subtracting a baseline target gas amount from a peak target gas amount in the store.

In one embodiment, the method further includes a step wherein the amount or concentration of the target gas is calculated by measuring an area under a concentration data curve over time from release from the store.

In one embodiment, the method further includes the step of extracting the gas from the store to a target gas sensor unit, for sensing the amount of target gaseous or aerosolized compound.

In one embodiment, the method further includes the step of conditioning a sample amount of the gaseous environment to a selected physical state to provide a conditioned gas sample for input to the separation step.

In one embodiment, the method further includes the step of sensing any one or more of the group consisting of oxygen, carbon dioxide, carbon monoxide or volatile organic compounds in the target gas sensing unit and/or the sample gas sensing unit.

In one embodiment, the method further includes a step wherein the conditioning step includes dehumidifying the gas sample.

In one embodiment, the method further includes a step wherein the separation step is conducted in a concentrator module, in which the store is disposed, to store a storage matrix.

In one embodiment, the method further includes a step wherein the storage matrix is activated carbon.

In one embodiment, the method further includes a step wherein ethylene is the target gas and the separation step is adsorption of ethylene.

In one embodiment, the method further includes a step wherein the sensing step includes desorption from the store of, and sensing in the target gas sensor of, ethylene.

In one embodiment, the method further includes a step wherein the sensing step includes sensing of a second gas component such that the conversion step includes adjustment of the concentration data by reference to a target sensor sensitivity to the second gas.

In one embodiment, the method further includes an assessment step in which the processor compares the amount or concentration of the target gas to a threshold level or rate of increase.

In one embodiment, the method further includes an alarm actuation step in which a wireless module transmits an alarm to a display or loudspeaker and amplifier on a mobile device or computer.

In one embodiment, the method further includes a step wherein the alarm step is taken if the threshold level or rate of increase is exceeded.

In accordance with another aspect of the present technology, there is provided a gas component monitor for monitoring the concentration of a target gaseous or aerosolized compound in a gaseous environment, the monitor system including:
- a pump for extracting from an environment a sample of gas of a selected or predetermined quantity from the environment;
- a concentrator module which includes a separator for separation of the target gaseous or aerosolized compound from the gas sample, the separator including a store for storage of a target gaseous or aerosolized compound;
- a target gas component sensor module for sensing the concentration or amount of the gaseous or aerosolized compound in the store; and
- a processor connected to the target gas component sensor module, the processor configured to calculate the environmental concentration of the target gaseous or aerosolized compound based on a conversion algorithm.

In one embodiment, the processor is configured to receive data relating to properties of, and the amount of, sample gas.

In one embodiment, there is provided a meter for measuring a mass or other physical quantity, for determining the amount of the sample gas.

In one embodiment, the algorithm takes into account the data from the meter relating to the amount and other physical properties of, the sample gas, and the concentration or amount of target gas.

In one embodiment, there is further included a decanter to release the target gas from storage.

In one embodiment, the monitor further includes a conditioning module for conditioning a sample amount of the gaseous environment to a selected physical state to provide a conditioned gas sample.

In one embodiment, the conditioning module and the concentrator module include a conditioning chamber for receiving gas, and a dehumidifier including a temperature modulation element.

In one embodiment, the temperature modulation element and the concentrator module include a heating and/or element disposed in a block in a wall of the conditioning chamber.

In one embodiment, the store includes a storage matrix for storing the gaseous or aerosolized component.

In one embodiment, the storage matrix includes activated carbon.

In one embodiment, the store includes a foam element or tube in which to hold the activated carbon.

In one embodiment, the activated carbon is in granular form.

In one embodiment, the target gas component sensor module includes two ore more of the group consisting of ethylene, oxygen, VOC, carbon dioxide and carbon monoxide sensor elements.

In one embodiment, the conditioning module includes a drain and an exhaust.

In one embodiment, the technology further includes a wireless module for wireless communication of data with a mobile device.

In one embodiment, the technology further includes a controller on the mobile device for controlling any one or more of elements of the pump, separator, concentrator, conditioner or sensor units.

In accordance with still another aspect of the present technology, there is provided a gas concentrator unit for increasing the concentration of a target gas in an environmental gas sample, the gas concentrator including:
- a sample gas receiving chamber for receiving a sample gas, the sample gas receiving chamber including a gas inlet;
- a sensor module for measuring physical properties of the sample gas inside the receiving chamber;
- a separator portion for separating and storing a target gas from the sample gas; and
- a decanter portion for releasing the target gas from the store.

In one embodiment, the separator portion includes a selected quantity of activated carbon for adsorbing a target gas.

In one embodiment, the decanter includes a heater for releasing the target gas from the store.

In one embodiment, the technology further includes a sensor module for sensing the target gas.

In one embodiment, the sensor module includes at least one of the following: ethylene sensor, carbon dioxide sensor, carbon monoxide sensor, and VOC sensor.

In one embodiment, the amount of adsorbed target gas, or the concentration factor of the system, may be modified by varying the quantity, temperature, pressure and/or the time of gas sample exposed to the activated carbon by means of the main controller.

In one embodiment, once a specified quantity of the sample gas has been exposed to the activated carbon, the heating element, which is configured to heat the activated carbon, heats the activated carbon to break the bond of the adsorbed target sample gas, which results in a target gas concentration effect within the concentrator unit (release phase).

In one embodiment, the flow controller is a mechanical pump capable of moving the gas sample through the system at a controlled rate.

In one embodiment, a main controller is provided to control gas monitoring, movement, concentration and sensing operations.

In one embodiment, the main controller includes a microcontroller with analogue and/or digital inputs to interface with the sensors.

In one embodiment, the heater element's temperature may be controlled during both adsorption and release phases of the concentration process. Temperature control of the carbon during the adsorbtion phase is beneficial as the gas sample adsorbtion rates can be impacted by temperature and humidity, and control of such will increase the accuracy of the system.

In one embodiment, the concentrator unit includes a gas sample temperature and/or humidity and/or pressure sensor, which is configured to connect to the main controller.

Sensor readings from said sensors are connected to the main controller, and calibrations may be made to gas readings to account for changes in absorption or release rates due to sensed gas conditions.

In one embodiment, the flow controller is controlled with influence from the readings from a gas flow sensor; this provides facility for more accurate control of gas flow rates in the system and improves overall gas sensing accuracy.

In one embodiment, mass flow may be varied by changes to the volumetric flow rate of the flow controller. In an alternative embodiment, changes to mass flow may be obtained by increasing the duration of phases, such as the number of seconds that the adsorption phase or release phase last for.

In one embodiment, the gas analysis reading can be obtained by combining the ethylene sensor and offsetting it with offsets or multiplication factors based on the readings from any combination of the other sensor readings in the system. As one example, the ethylene reading could be obtained by taking the ethylene sensor reading, and providing a calibration offset based on the carbon monoxide detected in the sample, in order to calculate a more accurate ethylene reading. This is advantageous as some ethylene sensor readings may also be impacted by carbon monoxide gas, and the present invention could be used to remove such inaccuracies in the ethylene reading.

In one embodiment, an automatic calibration system is employed, comprising the taking of a number of measurements based on various concentrations multiples, wherein the concentration multiple is controlled by the main controller by varying the quantity of gas that is exposed to the concentrator prior to each gas analysis, and a calibration curve of sensor readings vs concentration multiple is obtained (FIG. 9). An interception of the calibration curve with the Y axis may then be mathematically determined to calculate a calibration offset, described below in detail, and said calibration offset may be applied to ethylene readings to increase accuracy and reduce sensor drift inherent in typical electrochemical sensors.

In an alternative embodiment, and as part of an automated calibration step, a known gas sample, such as from a calibration gas canister or other generated means, is passed through the gas analysis unit, and gas sensor readings can be compared with the known gas sample concentrations, and any variations in readings between measured and known values may be incorporated to make adjustment from future gas sample readings in order to improve accuracy.

In one embodiment, an automatic concentration overload detection system is employed in order to prevent damage or inaccuracy of the gas analysis sensors. This comprises taking a first measurements based on a low (or no) concentration multiple, wherein if it is determined that the gas sample is further concentrated a sensor overload may occur, higher concentration steps may not be completed and an error message generated.

In one embodiment, the automatic concentration overload detector consists of reading the carbon monoxide sensor (or an alternative sensor), and abandoning the measurement if concentrations are higher than a preferred threshold.

The sensor unit is in fluid connection to the outlet, where the used gas sample is exhausted back into the atmosphere.

In accordance with one aspect of the present invention there is provided a ripening monitor for produce which includes a gas sensing unit upstream or downstream from a gas sample heating unit.

Advantages

Advantageously, the system and method of embodiments can be used generally to detect the amount of a gas of interest in a sample mixture at concentrations well below the gas sensor's capacity to accurately detect that gas. Essentially the embodiments of the system and method amplify the gas signal to levels at which a gas sensor best operates, thereby improving accuracy. This kind of amplification is useful to use in a ripening monitor.

Another advantage is that the system and method of embodiments corrects for the influence of collateral gases on the monitoring of the gas of interest.

Still another advantage is that the monitor is able to provide feedback to users on their computers and/or mobile devices, about the ripeness of fruit so they can reduce wastage. Also, the system advantageously allows users to optimize ripeness of produce which may be stored in containers, and hence unable to be easily inspected, in preparation for sale.

Clarifications

In this specification, where a document, act or item of knowledge is referred to or discussed, this reference or discussion is not an admission that the document, act or item of knowledge or any combination thereof was at the priority date:
  (a) part of common general knowledge; or
  (b) known to be relevant to an attempt to solve any problem with which this specification is concerned.

It is to be noted that, throughout the description and claims of this specification, the word 'comprise' and variations of the word, such as 'comprising' and 'comprises', is not intended to exclude other variants or additional components, integers or steps.

When the word "correction" or "adjustment" or "conversion" is used in this specification and claims it refers to a process where parameters are applied to a target gas concentration reading, and wherein the parameters may be determined either as part of a measurement, as part of a periodic calibration process, or once during factory calibration, in order to improve the usefulness of the target gas concentration readings.

BRIEF DESCRIPTION OF THE DRAWINGS

In order to enable a clearer understanding, a preferred embodiment of the technology will now be further explained and illustrated by reference to the accompanying drawings, in which.

DETAILED DESCRIPTION OF AN EXAMPLE EMBODIMENT

Figure 1:
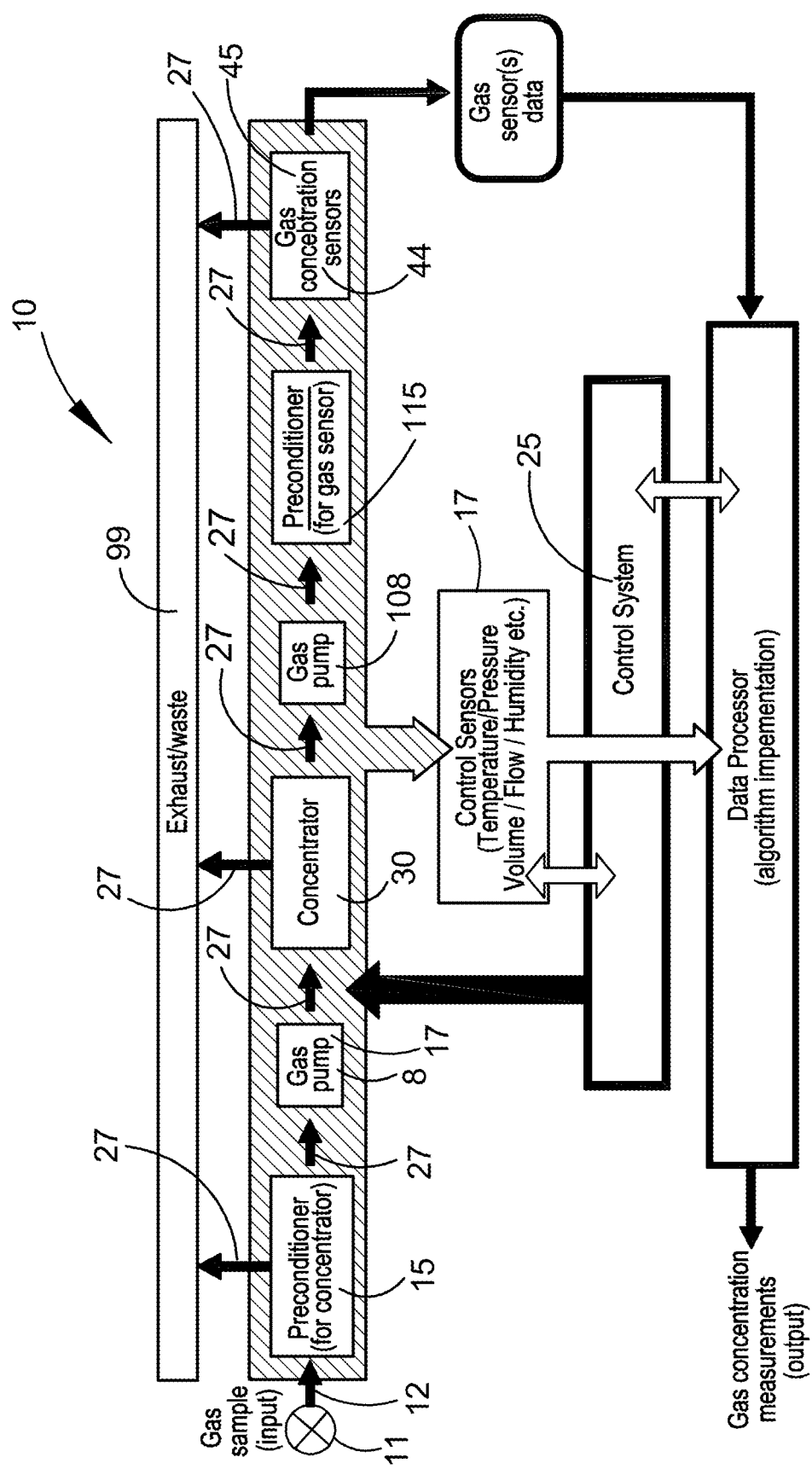
FIG. 1 is a schematic view of a gas monitoring system in accordance with an embodiment of the present technology.

Referring to the drawings there is shown an embodiment of gas monitoring system generally indicated at 10. The architecture of one ripening monitor system 10 is shown schematically in FIG. 1, and the structural details of each of the technical components in the architecture are shown in FIGS. 2, 3, 4, 5, and 6. Another embodiment of ripening monitor system is shown at 110 in FIG. 7. Like numerals on that Figure denote parts like other embodiments, for efficiency of description.

Figure 8:
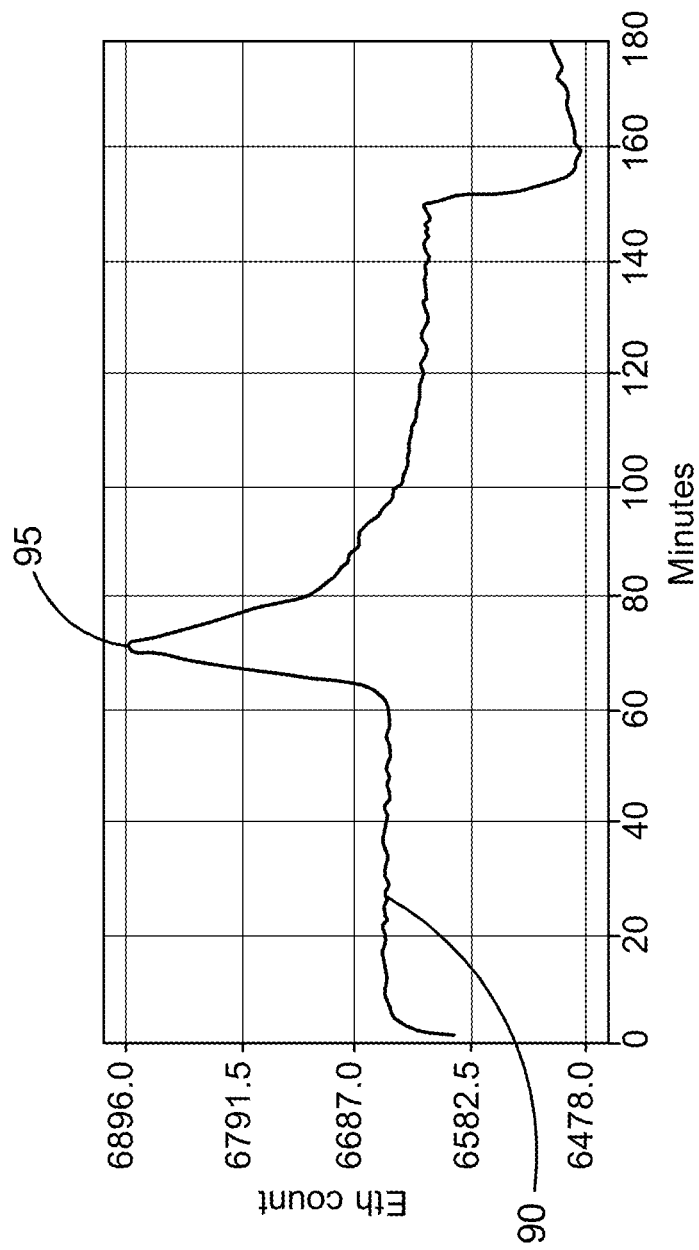
FIG. 8 is a graph of results of a test conducted with an embodiment of the present invention showing ethylene desorption results from a target gas sensor.
Figure 9:
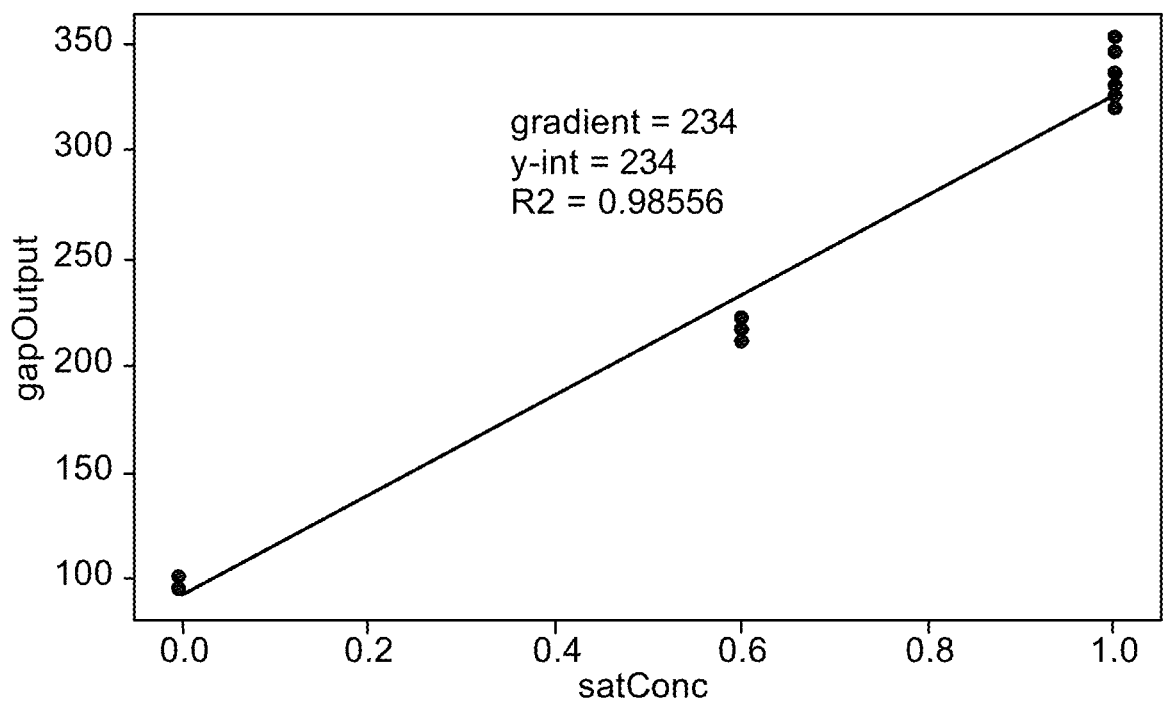
FIG. 9 is a graph showing conversion of the target sensor output to convert to environmental concentration of ethylene.

Output of a target gas sensor of the system is shown in FIG. 8, and an example of a conversion algorithm based on a selected concentration is shown in graphical form in FIG. 9. FIGS. 10 to 14 show correction of results based on the amount of one collateral gas, it being carbon monoxide.

In FIG. 1, there is shown a schematic diagram of a gas monitoring system generally indicated as 10. There is shown a conditioning unit 15, a pump 8, a concentrator 30, a second gas pump 108, a second conditioner 115, a sensor module 44 and a main controller 25. These are described in detail below, sometimes overlapping with FIG. 7 and the flowcharts in FIGS. 14, 15 and 17.

Conditioner Module

The conditioner module is described herein, but it is to be understood that it is an optional feature of the technology.

Control of the gas sample air temperature, humidity and pressure provides the advantage of preventing condensation (that may affect gas sensor response downstream), as well as reducing the measurement variables to provide a more accurate gas component reading on a target gas sensor.

To that end, it can be seen that the system 10 provides an inlet 12 for receiving a gas sample from either a bottle of purified aerosolized or gaseous compound or mixture or from the environment in a chamber such as the interior of a room, building, toilet cubicle, or ambient atmosphere, shipping container or trucking container or refrigerator or produce storage room or cool room, or from a combination of the above (all not shown). This received gas sample is conditioned in one or two conditioner modules described below, and analyzed downstream of those conditioner modules to assess the concentration of the target gas.

The inlet 12 is in fluid communication with a conditioner module 15, a flow control module 17 and/or pump 8, depending on the embodiment being discussed. Any one of those elements may include a valve 11 connected to the inlet 12, and one of a wide variety of mechanical pumps 8 capable of moving the gas sample through the system at a controlled rate, with or without a regulator (not shown). One type of pump 8 contemplated is a peristaltic pump, and another type of pump contemplated is a piston pump. Other types of pump 8 are contemplated as being of utility in the system include diaphragmatic pumps, and balloon pumps, screw pumps and others that can transfer gas from one place to another in a controlled fashion.

Figure 2:
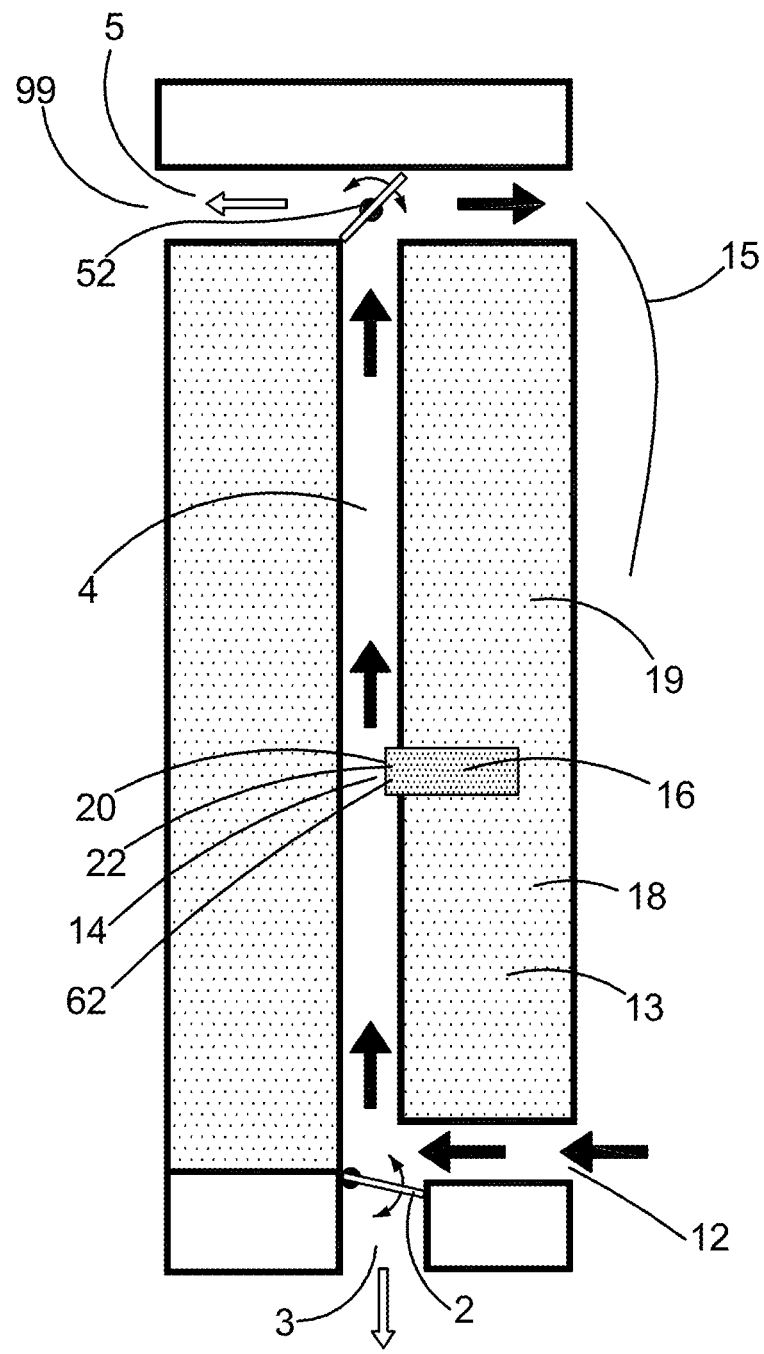
FIG. 2 is a schematic view of the conditioning unit for use with the gas monitoring system of FIG. 1.

The conditioning module 15 includes a tube or chamber 4 into which a sample gas is introduced for conditioning. FIG. 2 shows one possible embodiment of the conditioning module 15.

The conditioning module 15 further includes a temperature modulation module 13 disposed in the walls of the tube or chamber. The temperature modulation module includes a heater element 18, and a Peltier cooler 19.

There is an exhaust outlet 5 disposed in the conditioning module chamber 4 to remove gas. There is also a drain 3 for removal of water and excess moisture and/or ice. The exhaust outlet 5 and drain 3 may be provided adjacent a valve 52 and 2.

The temperature modulation module 13 further includes a sensor module 16 which includes a temperature sensor 20, a humidity sensor 22, a flow sensor 14, pressure sensor 62 and which also may include an agitator (not shown) to facilitate the mixing of the gas undergoing pre-conditioning.

In operation, the conditioner, which is connected to the main controller 25, is caused by the main controller 25 to actuate the Peltier cooler 19 to freeze the water in the sample gas in the chamber 4 to reduce the humidity, and then warming at least a portion of the walls of the chamber 4 by actuation of the heating elements 18 and opening valve 2 as part of a defrost cycle to drain the water from the conditioner module 15.

Main Controller

There is provided a main controller 25 for, among other things, controlling the conditioning of the sample gas. The main controller 25 includes a microcontroller, in one form being a 32-bit ARM microprocessor, with analogue or digital inputs, and for conditioning the sample gas it is configured to interface with the sensor module 16 and the temperature modulation module 13 and the flow control module 17, or in some embodiments, pump 8.

Data connections are made between the sensor module 16, the temperature modulation module 13, the flow control module 17, or pump 8, and the main controller 25. The data connections may also be wireless or optical or indeed any suitable connections for sending data.

One of the other tasks of the main controller 25 is to control the temperature and humidity in the conditioning module 15. In operation, data from the sensor module 16 is provided to the conditioning controller 25, and corrections may be made to final gas component readings to account for gas conditions sensed by the sensor module 16.

Hoses

Between the conditioning module 15 and other components described herein, there are gas transport hoses 27 connected with barbed attachments and O-rings (not shown) so as to transport the gas and aerosolized compounds and mixtures.

The transport hoses 27 connect so as to transfer the sample gas from the conditioning module 15 to a concentrator module 30 which is identified on the Figures (at least FIGS. 1 and 2), downstream from the conditioning module 15.

Concentrator Module

Figure 3:
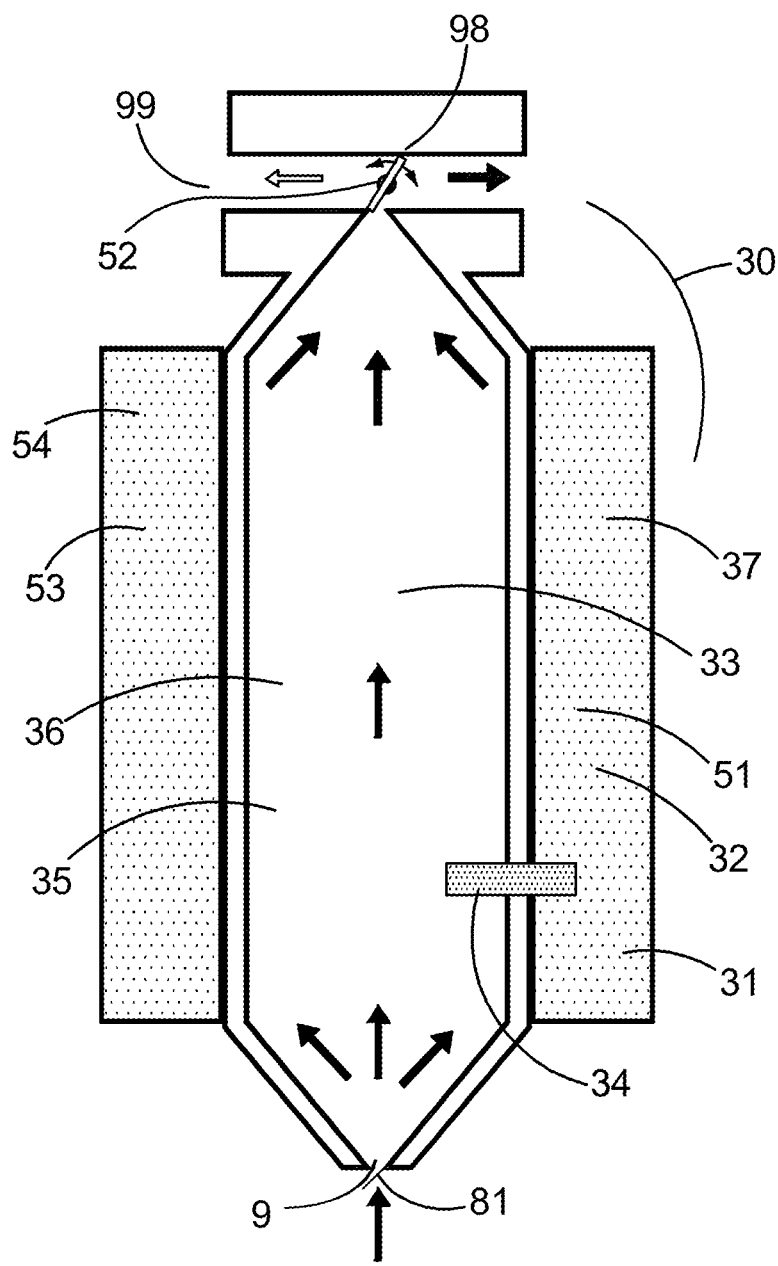
FIG. 3 is a view of the concentrator unit for use with the monitoring system shown in FIG. 1.

A concentrator module 30 shown as part of the system 10 in FIG. 1 and in detail in FIG. 3, has a gas chamber 33 configured to receive the sample gas from the conditioning module 15 through inlet 9. The concentrator module 30 further includes a heater 32, a chiller 31, and a temperature, humidity and pressure sensor module 34. Inside the gas chamber 33 is provided a separator 35 in the form of a gas adsorption unit 36, being activated carbon.

The concentrator unit 30 is configured to receive the gas sample (conditioned or not, depending on the embodiment being discussed) through the inlet 9, such that in operation, a gas component of interest, in this case, ethylene, can be adsorbed in the activated carbon of the separator 35 as part of an adsorption process.

In operation, the amount of adsorbed target gas component, (related to the concentration factor of the system), may be modified by varying the mass flow of the gas sample that passes over the activated carbon 36 by means of the main controller 25 and flow controller 17 or pump 8, or by the heat, humidity and other conditions in the conditioner 15. Once a selected mass of the sample gas has passed over the activated carbon in the separator 35, the controller 25 causes the inlet 9 to close, and/or the inlet valve 81 to close, and then heater 32, configured to heat the activated carbon in the separator 35, heats the activated carbon to break the bond of the adsorbed target gas, which results in a gas concentration effect within the concentrator unit 30. This is referred to as a decanting or release phase.

The heater 32 is in the form of a temperature controlled outer layer or block 37 in which there is disposed an embedded heating element 51, a cooling element 53 and a temperature sensor 52. The cooling element is a Peltier element 54. As with the conditioning module 15, data connections are made between the main controller 25 and temperature sensors 34 and the heater 32. The main controller 25 is configured to vary electrical power supplied to the heater 32 such that the activated carbon can be maintained at a preferred temperature during the gas release phase. The main controller 25 is also configured to vary electrical power supplied to the chiller 31, which is done after the gas release phase to prepare for another adsorption cycle.

The heater's temperature is configured to be controlled during both adsorption and release phases of the concentration process. Temperature control of the carbon during the adsorption phase is beneficial as the gas sample adsorption rates can be impacted by temperature and humidity, and control of such will increase the accuracy of the system.

Corrections may be made to gas readings at the end of the detection process, described below, to account for changes in adsorption or release rates due to sensed gas conditions in the conditioning module 15 or in the concentrating module 30, or in the secondary conditioning module 115.

The flow controller 17 or pump 8 (in another embodiment) is controlled with influence from the readings from a gas flow sensor 14; this provides facility for more accurate control of gas flow rates in the system and improves overall target gas sensing accuracy.

In an embodiment that is not shown, a flow controller may be placed downstream of the concentrator unit or sensor unit. Mass flow may also be varied by changes to the volumetric flow rate of the flow controller 17 or by the pump 8. Changes to mass flow may be obtained by increasing the duration of phases, such as the number of seconds of the adsorption phase or release phase.

A check valve is in fluid communication with the inlet so that gas samples may only flow one way through the system, thus preventing contamination of results by double-measuring the same sample of gas.

In one embodiment the separation could include CO2 scrubbing by using a membrane and in that embodiment the store would be a separate storage chamber (not shown) to the side or end or at least adjacent to the chamber 33.

Sensor Conditioning Module

A sensor conditioning module 115 which is similar to the conditioning module 15 is provided in the embodiment shown in FIG. 1 to facilitate providing the sensors in the analysis module with sample gas within selected parameters for more accurate sample gas component readings.

In this embodiment, when provided and in use, the sensor conditioning module, which looks similar to conditioning module 15, receives target gas from the release or decanting phase from the concentrator 30. In use, the sensor conditioning module 115 is instructed by the main controller 25 to cool the sample gas down to a selected temperature by actuating Peltier elements, so that the target gas sensor reads the gas in its most sensitive zone.

The sensor conditioning module 115 also includes a pump 108 to transfer the conditioned sample gas to the analysis module 44.

As with the conditioning module 15, there is provided an exhaust outlet and a drain outlet for water and moisture and ice.

Sensor Module

Figure 6:
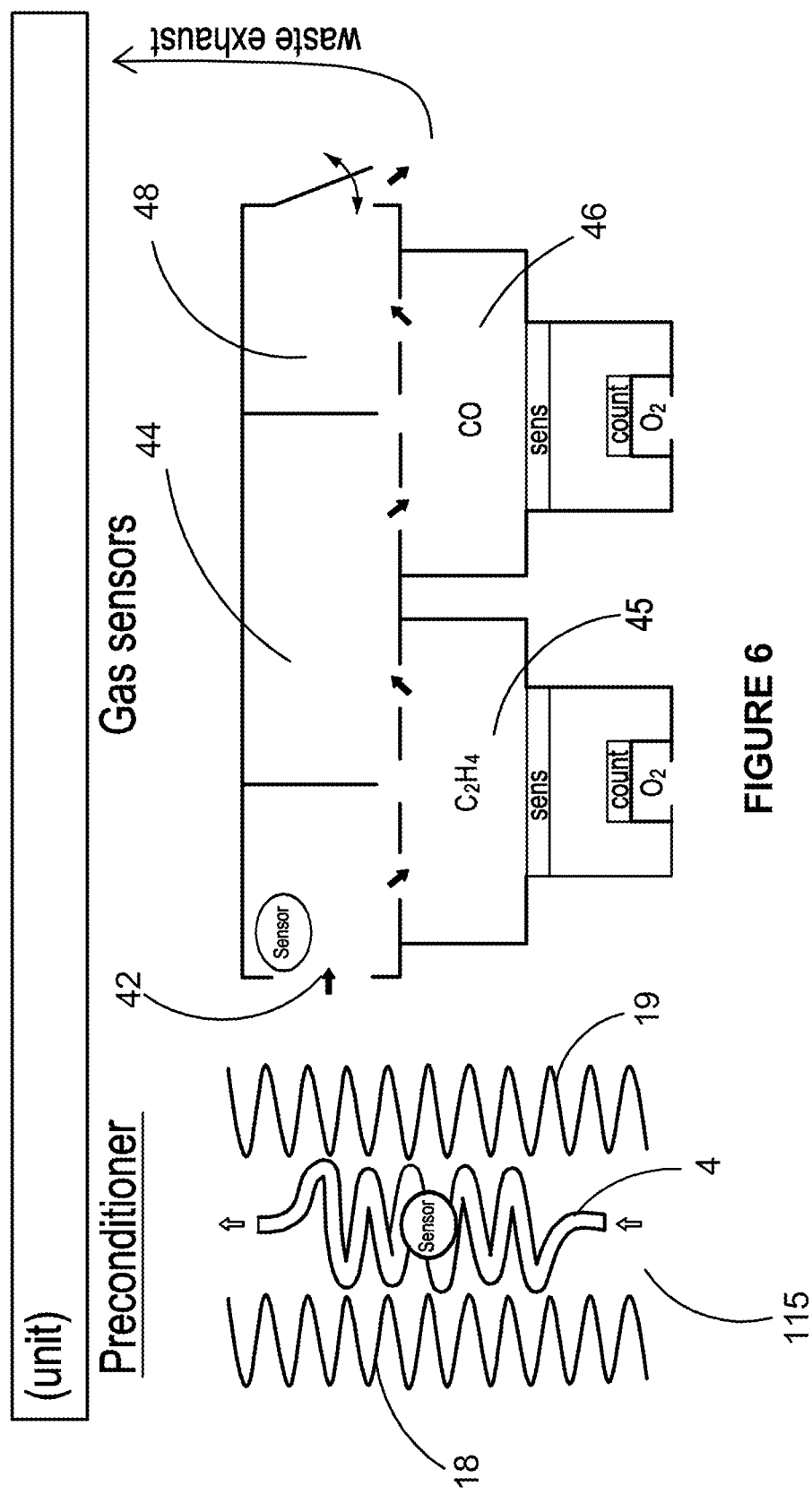
FIG. 6 is a schematic view of the conditioned and gas sensor units shown in FIG. 1.
Figure 7:
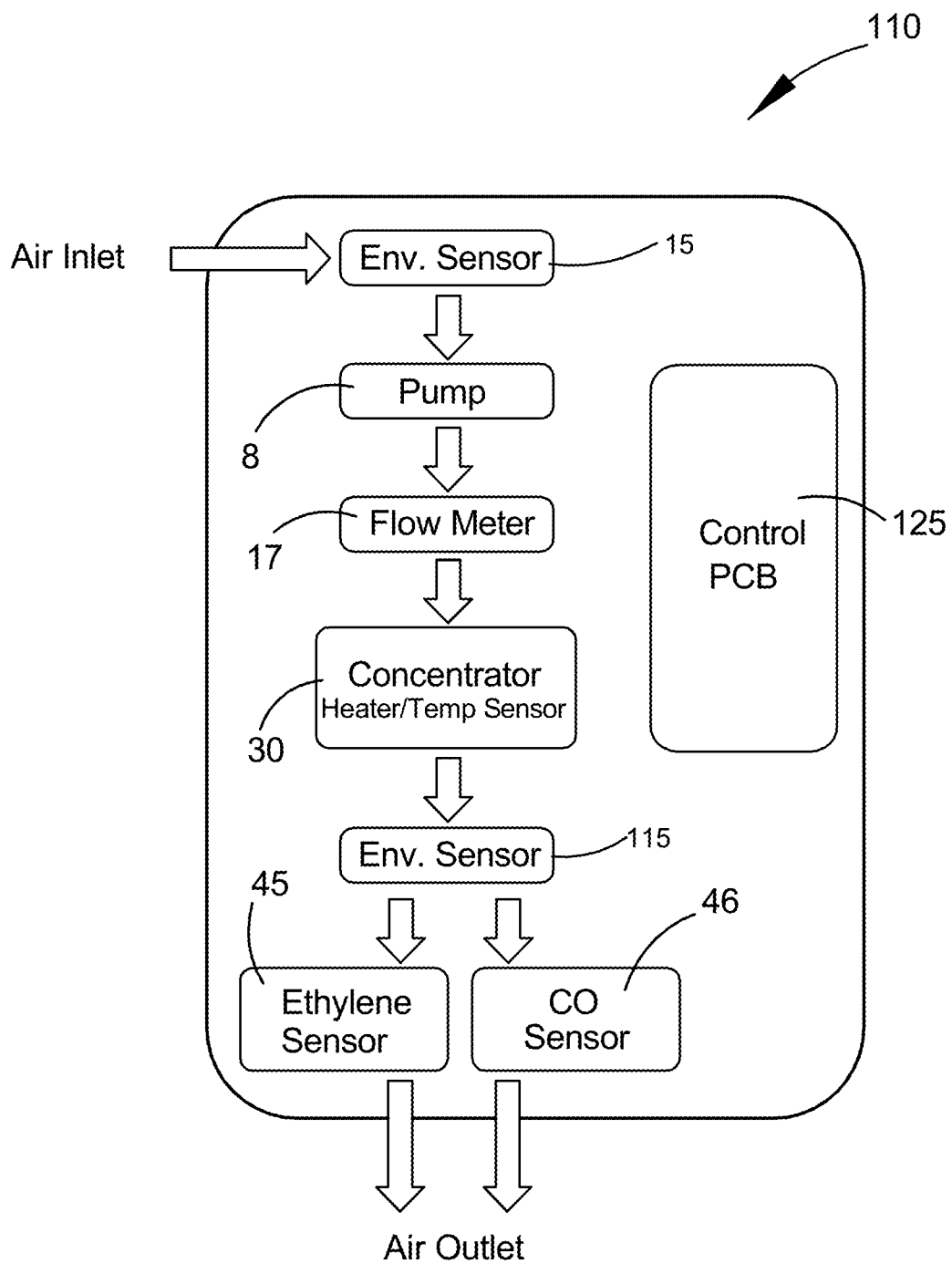
FIG. 7 is a schematic view of a gas monitoring system in accordance with an embodiment of the present invention.

Reference is made to FIG. 6. Inlet 42 is in fluid communication with analysis chamber 44 which receives sample gases and puts them into contact with carbon monoxide sensor 46, Ethylene sensor 45 and a temperature, pressure and humidity sensor unit 48. The analysis chamber 44 is shown as passing the sample gases sequentially between these sensors (Temp/pressure/humidity unit, ethylene, CO) but there could be a sinuous chamber, or the sensor units could be arranged in parallel with the others in one common analysis chamber 44, say, around the outside of it, so that there is a simultaneous reading of all component gases from the one sample.

The sensors 45, 46, and 48 are connected to the main controller 25 so as to transfer data thereto, either wirelessly or in a wired or other suitable way (such as optically if suitable). The connections are so that the controller 25 can provide central monitoring of the analysis process for multiple gas concentrations simultaneously, and apply any one of a plurality of correction regimes during and before and after analysis as described below.

Main Controller

The target gas result can be obtained by transmitting data from the ethylene sensor 45 into the main controller 25. The main controller 25 displays the results on a display (not shown).

To obtain a more accurate result, the gas component reading can be refined by combining the ethylene sensor 45 and correcting it with offsets or multiplication factors based on the readings from any combination of the other sensor readings in the system. As one example, the ethylene reading could be obtained by taking the ethylene sensor 45 reading, and providing a correction offset based on the carbon monoxide detected in the sample, in order to calculate a more accurate ethylene reading. This is advantageous as some ethylene sensor readings may also be impacted by carbon monoxide gas, and the present invention could be used to remove such inaccuracies in the ethylene reading.

This is done by for example,

An automatic calibration method is employed, comprising the steps of taking of a number of measurements based on various concentration multiples, wherein the concentration multiple is controlled by the main controller 25 by varying the mass flow past the concentrator prior to each gas analysis, and a calibration curve of sensor readings vs concentration multiple is obtained. An interception of the calibration curve with the Y axis may then be mathematically determined to calculate a calibration offset, and that calibration offset may be applied to ethylene readings to increase accuracy and reduce sensor drift inherent in typical electrochemical sensors.

In an alternative embodiment and as part of an automated calibration step, a known gas sample, such as from a calibration gas canister or other generated means, may be passed through the gas analysis unit 44, and gas sensor readings can be compared with the known gas sample concentrations, and any variations in readings between measured and known values may be offset from future gas sample readings in order to improve accuracy.

Overload Detection

An automatic concentration overload detection method is employed in some embodiments to prevent damage to, or inaccuracy of, the gas analysis sensors 45 and 46. This feature includes the steps of taking a first measurement based on a low (or no) concentration multiple, wherein if it is determined that the gas sample is further concentrated a sensor overload may occur, higher concentration steps may not be completed and an error message generated.

The automatic concentration overload detection method consists of reading the carbon monoxide sensor (or an alternative sensor), and abandoning the measurement if concentrations are higher than a preferred threshold.

The sensor unit 40 is in fluid connection to the outlet 61, where the used gas sample is exhausted back into the atmosphere.

The system can be mounted in a housing and placed inside a chamber in which is disposed ripening produce.

The controller 25 includes a memory, processor, I/O port for data transfer and therefore can be programmed to implement control of gas measurement steps and calibrations, and monitoring of the desired atmosphere (not shown).

The calibration cycles and regimes can be programmed into the controller 25 for routine implementation, or when one gas is measured as being off design, or any one of them can be manually actuated by a remote controller such as for example, a mobile device.

The main controller 25 may connect to a central database server and upload data relating to the gas concentrations, and hence ripeness of fresh produce. The server may then process this data, and provide feedback to users on recommended actions via alerts (such as via SMS messages, push notifications, emails, or recorded phone messages), such that users of the system can reduce produce wastage due to over ripening.

Connection to the database server may be achieved via wired or wireless connection to the internet, or via connection through a third party device (such as via WiFi connection to a smartphone, wherein the smartphone connects to the internet over a 3G/4G/5G connection).

System users may also input into the database, such as via an internet-connected smartphone App (shown on FIG. 16), physical observations of fruit ripeness and condition. This data may then be processed in conjunction with previously collected gas sample data, in order to develop optimal algorithms for determining recommended actions. In one embodiment, optimal algorithms may be determined with the use of artificial intelligence and/or machine learning systems.

Example Method

Conditioning

Figure 4:
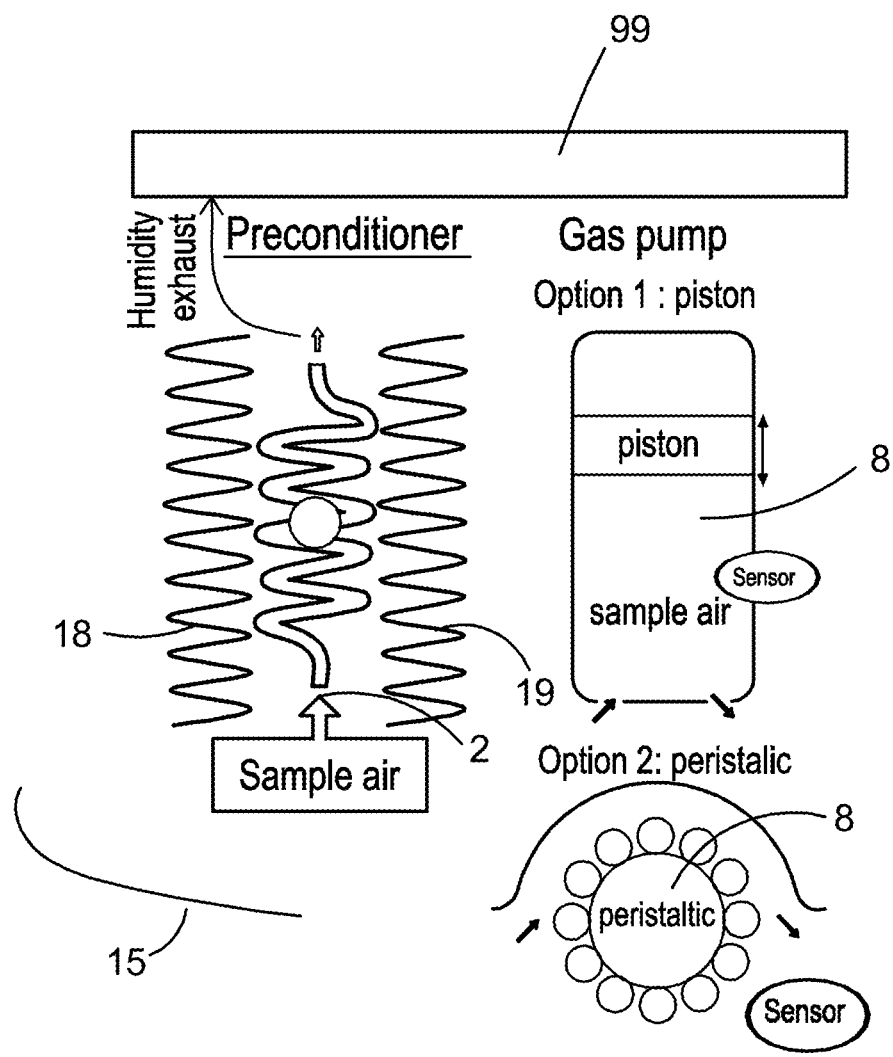
FIG. 4 is a schematic section view of the conditioning and pump units for use with the gas monitoring system shown in FIG. 1.
Figure 5:
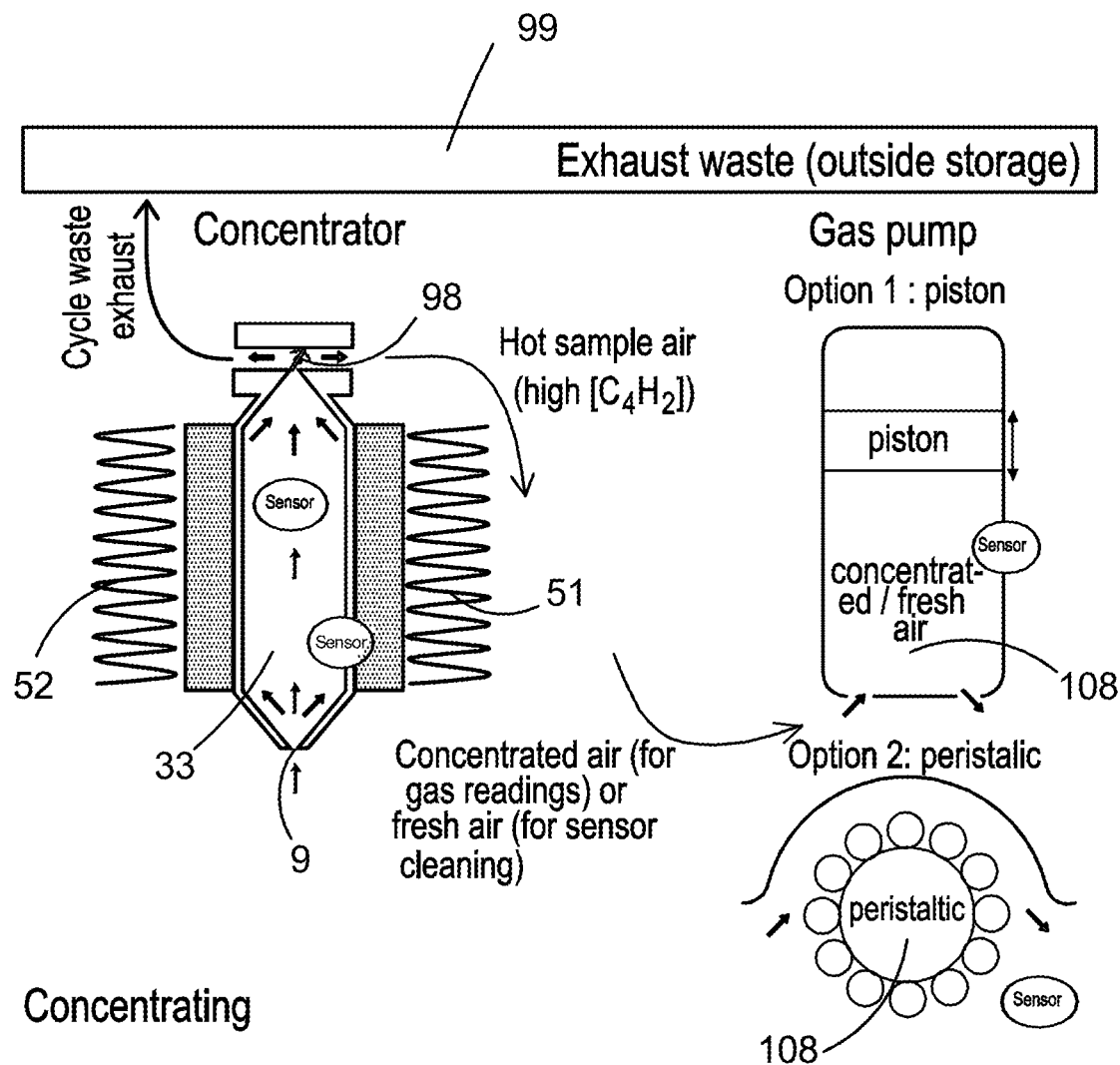
FIG. 5 is a schematic view of the concentrator and pump units for use with the gas monitoring system shown in FIG. 1.

Again, the conditioning step is described here, but as an optional step. Turning to FIG. 4, (and the steps in FIGS. 14, 15 and 17) there is shown the conditioner 15 and pump 8.

In one particular version of the present method and technology, there is provided a batch processing method. This batch processing method is described below. The continuous processing method is described in relation to FIG. 7, where a flow meter 17 and pump 8 drive and monitor the sample gas through the system for a selected period of time (say, 30 minutes or 1 hour). It is to be understood that the steps in FIGS. 14, 15 and 17 apply equally to the continuous processing method, not just the batch processing method.

A sample gas conditioner 15 draws in a gas and holds it until it meets the right conditions. (Step 500 in FIG. 14, 600 in FIG. 15, 700 in FIG. 17)). First, there is provided a fixed quantity of sample gas. The way the controller becomes aware of the quantity of the gas is that it may be measured by a gas sensor (Step 710 in FIG. 17), or it may be pre-programmed into the controller 25, (since it may know the volume in a pump 8 and its revolutions or cycles utilized) or the quantity of sample gas is controlled by a feedback controlled gas pump, either a piston pump or a peristaltic pump. The main controller 25 actuates the Peltier device 19 and the temperature is caused to be dropped to below zero. (Step 610 in FIG. 15, Step 720 in FIG. 17). This freezing step reduces humidity in the sample gas in the chamber 4, and periodically then the main controller 25 actuates the heating element 18 and opens valve 2 which removes condensed water.

Concentrating/Separating

Figure 14:
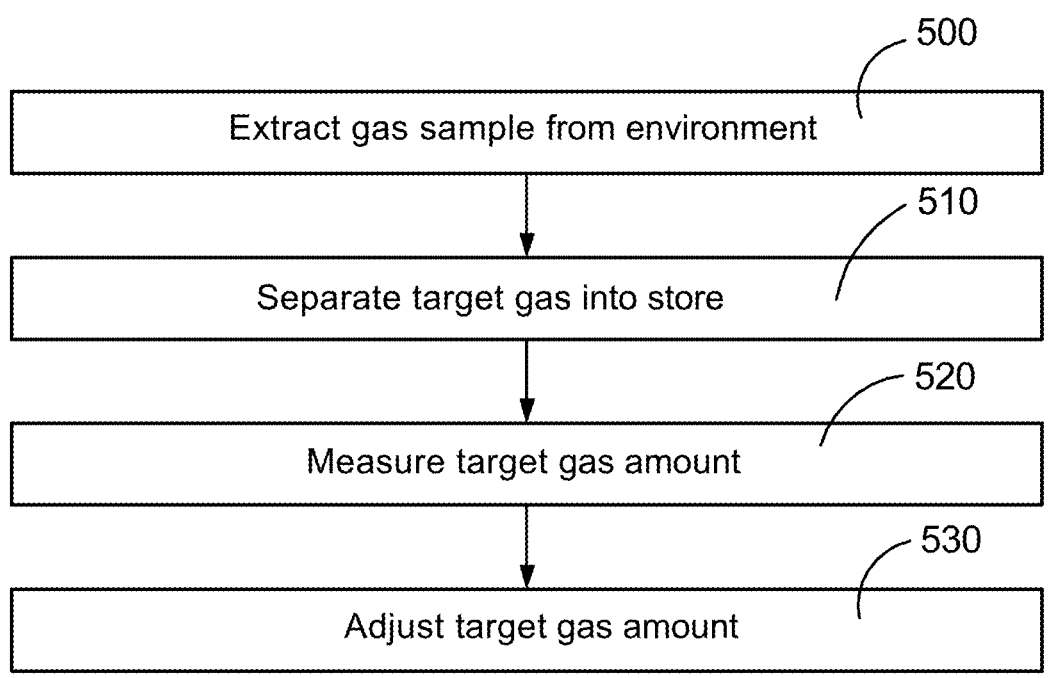
FIG. 14 is a flow diagram showing method steps taken in an embodiment of the present technology.
Figure 15:
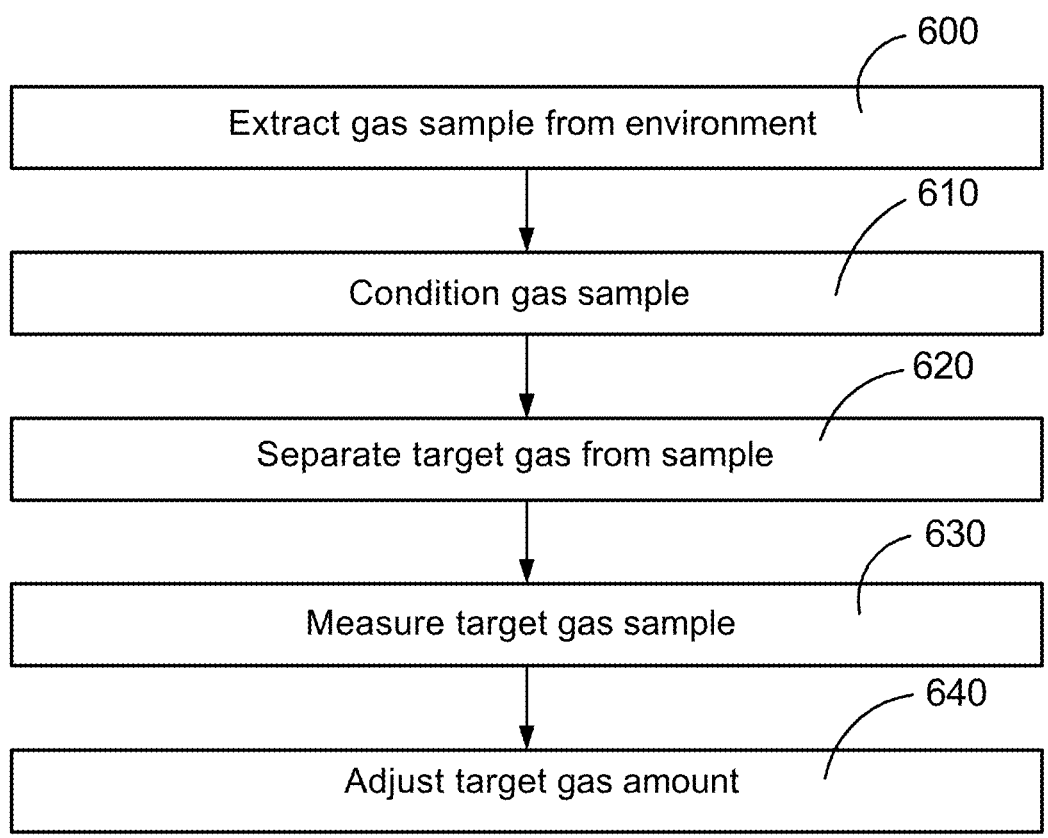
FIG. 15 is a flow diagram showing method steps taken in an embodiment of the present technology.
Figure 17:
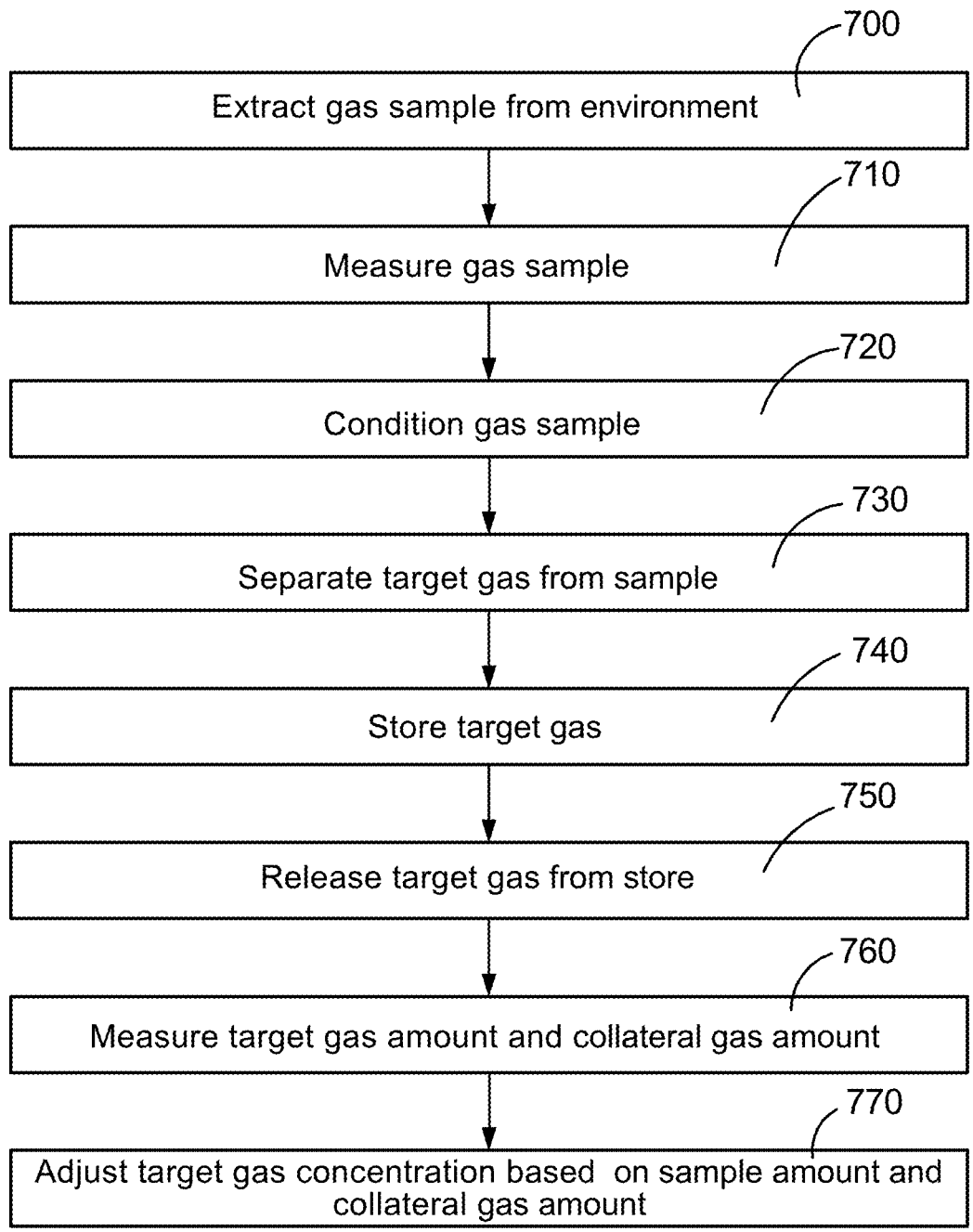
FIG. 17 is a flow diagram showing method steps taken in an embodiment of the present technology.

The target gas ethylene in the chamber 4 is transferred by pump 8 and concentrated via a separation method called carbon adsorption (Step 510 in FIG. 14, Step 620 in FIG. 15, Step 730 in FIG. 17). There may be in one embodiment, several phases.

First, there is a separation/adsorption/store cycle (Step 740 in FIG. 17). In that cycle, 1.5× concentrator volume of cold gas (at sub zero temperature) is pumped through the concentrator 30 to ensure complete volume exchange. The excess gas is released into the exhaust 99.

The main controller 25 holds a valve 81 at the inlet 9 and an outlet valve 98 in the concentrator closed for a selected time, while it opens the valve 2 in the conditioner to prepare another sample quantity of gas. The pumping of sample gas and the holding cycles are repeated multiple times, and the excess gas is discarded into the cycle waste exhaust 99. The number of separation/adsorption/capture cycles is adjusted until gas readings are obtained within the midrange of the sensor 34.

Decant/Release Phase

On the last adsorption cycle, the main controller 25 actuates the heater elements 51 to heat the separator store 36 to a temperature that releases $C_2H_4$, but with minimal CO (~115 deg C.) (Step 750 in FIG. 17).

The concentrator outlet port 98 is opened to the gas pump 108. A pump permits hot gas extraction under a vacuum, which facilitates desorption, and extraction of gas without mixing from the previous chamber.

The main controller 25 causes the valve 98 to close.

Cooling Phase

The main controller 25 may actuate the Peltier units 54 so that the separator/concentrator is cooled down to a fixed sub-zero temperature in preparation for the next phase of adsorption/capture cycles. This reduces the humidity in the separator/concentrator.

Gas Sensor Conditioning and Pumping $C_2H_4$ is stored in the sample chamber and/or conditioner tubing until cooled to a fixed temperature (20 deg C.) in preparation for the gas sensors. When the gas reaches 20 deg (actively controlled), it is expelled across the gas sensors for 3 minutes at atmospheric pressure. The pump 8 is feedback controlled that ensures the gas passes the sensors at atmospheric pressure for 3 minutes.

Two pumping options are possible; a piston pump permits volume changes as the gas changes temperature and has greater volume control over gas quantities than compared to a peristaltic pump.

Sensor Reading and Cleaning Cycles

Once the sample air is 20 deg, it is directed past the sensor module 44 for 3 mins to obtain the reading. (Step 520 in FIG. 14, Step 630 in FIG. 15, Step 760 in FIG. 17). A tube exiting the gas sensor conditioner transfers gas into a sensor chamber which ensures the gas will pass through and equilibrate with the sensor's reservoir.

Three minutes of gas exposure is controlled by the gas pump (two options; piston pump preferred). A flap at the exit reduces backflow thereby improving one directional flow.

Following the reading cycle, fresh air is drawn by the gas pump, through the conditioner and into the gas sensor chamber for 10-30 mins to reset the sensor for improved sensor performance and lifetime.

In the reading cycle, the target sensor data is sent from sensor 45 and sensor 46 and 48 to the main controller 25. The main controller 25 records the ethylene count (target gas) as shown in FIG. 8. The baseline count recording can be seen at 90. During the release phase, the peak can be seen rising from the baseline 90 to peak 95 and then dropping back. The main controller 25 subtracts the baseline ethylene count from the peak to obtain a target gas ethylene reading of the sample. The main controller may also calculate the area under the curve (with the baseline being the base) from the moment the curve begins rising from the baseline 90 to the peak 95 to obtain the ethylene reading for the concentrated gas. This reading is accurate because it is essentially in a sweet spot for the target gas sensor.

The ethylene reading calculated may then be converted to account for the concentration of the sample. (Step 530 in FIG. 14, Step 640 in FIG. 15, Step 770 in FIG. 17).

To convert the ethylene reading from the target gas sensor to the environmental concentration, a conversion algorithm is prepared and/or solved in the processor. When the amount of sample gas and its conditions are preset and predetermined, the inventors have, surprisingly, and after much hard work, found that a simple graph (in practical terms, stored as a lookup table in the memory of the controller 25) such as that shown in FIG. 9 can be used as a conversion. FIG. 9 shows the relationship between the ethylene (target gas) sensor 45 reading (peak-baseline gap output calculation) and environmental gas concentration values.

GapOutput is on the Y-axis of FIG. 9 and it relates to the ethylene sensor 45 reading of the concentrated target ethylene gas, while satConc on the X-axis FIG. 9 is the environmental concentration of ethylene which correlates with that sensor reading. FIG. 9 is basically governed by the equation $y=mx+c$, where $c=92$, and $m=234$. So, doing the conversion using the algorithm, the environmental concentration when the ethylene reading is 0.2 ppm is 138.8. This conversion algorithm takes into account the performance of the concentrator at a range of ethylene concentrations.

Changing any of the quantities in the conditioner or concentrator gives you a different slope, y-axis intercept, etc, and a new conversion algorithm can be generated by the processor by receiving data from sensors measuring those quantities.

The ethylene reading calculated above may also be adjusted to account for humidity or pressure or other readings taken from sensor unit 48, or unit 16, or CO sensor 46, and one of those correction factors is CO and is described below and shown in FIGS. 10 to 14. The inventors have identified that ethylene sensors are sensitive to CO gas, and adjustment can be required. The inventors have also noted that CO sensors are sensitive to ethylene gas. The inventors have noted that the responsiveness or sensitivity of certain ethylene sensors to CO is about 8% and the sensitivity of certain CO sensors to ethylene is 50%.

Figure 10:
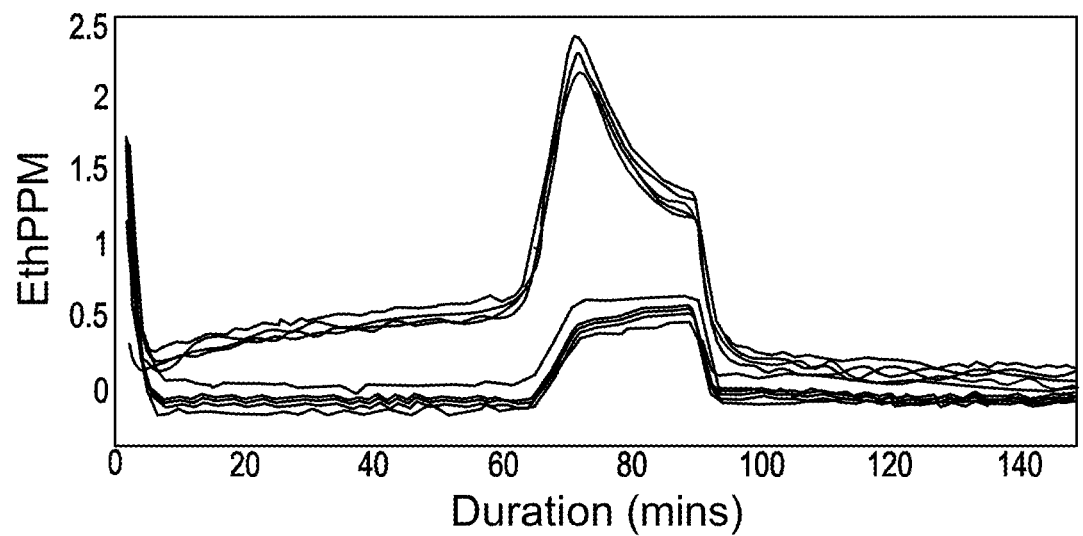
FIGS. 10 and 11 are graphs showing ethylene adjustment on the basis of the presence of carbon monoxide.
Figure 11:
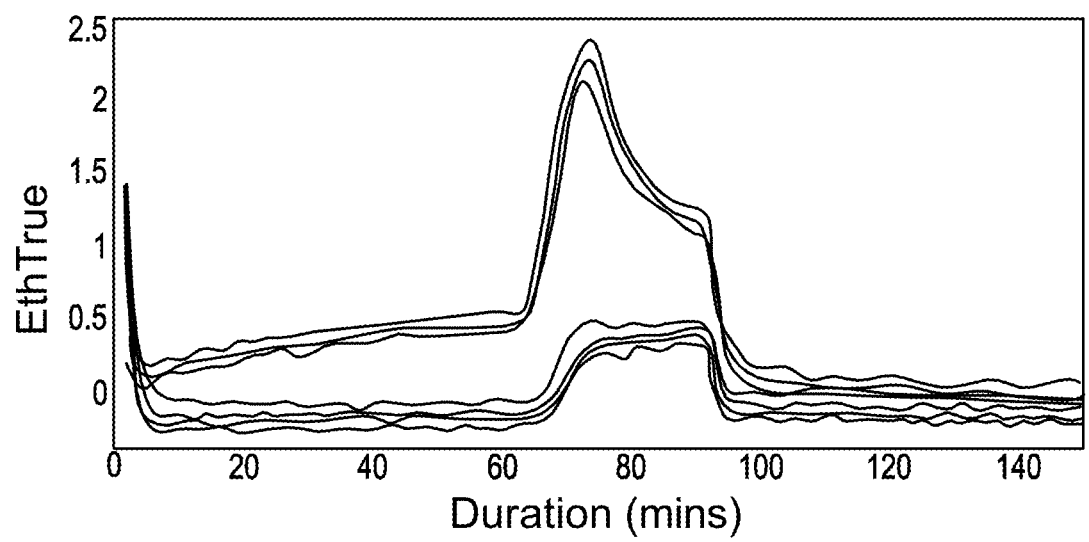
Figure 12:
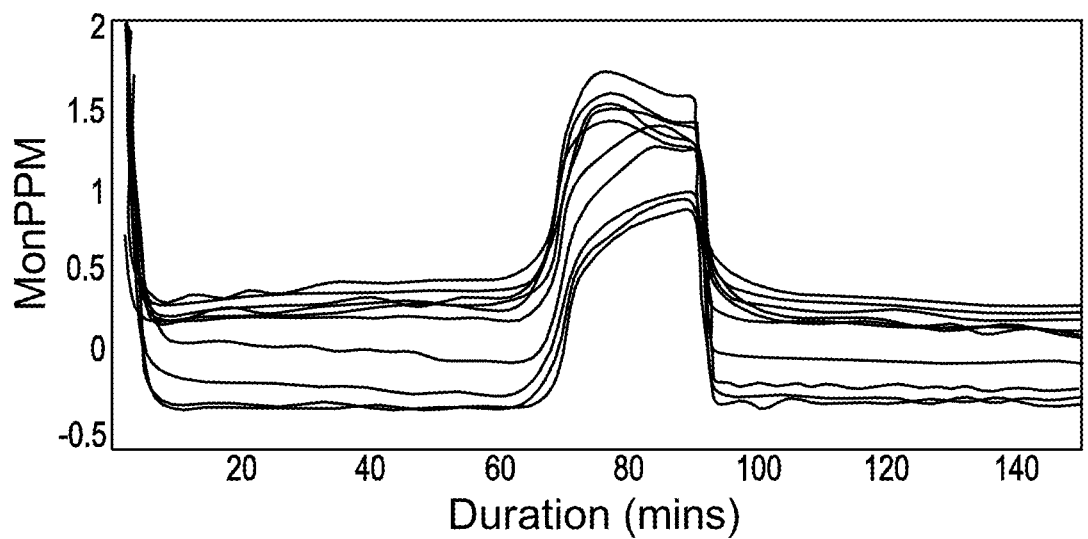
FIGS. 12 and 13 are graphs of carbon monoxide in the concentrated sample gas.
Figure 13:
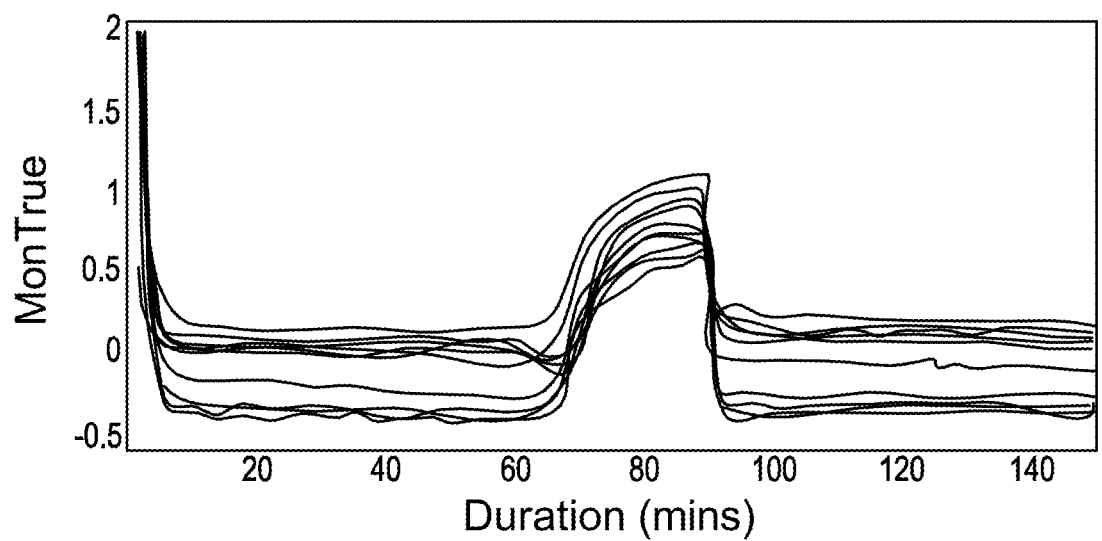

FIG. 10 is a graph showing the ethylene concentration in ppm measured over time. FIG. 11 is a graph showing the ethylene concentration after adjustment on the basis of the presence of carbon monoxide. FIG. 12 is a graph showing the carbon monoxide concentration in ppm measured over time. FIG. 13 is a graph showing the carbon monoxide concentration in the sample gas after adjustment on the basis of the presence of ethylene.

To resolve this, the two sensitivities can be quantified by solution to the simultaneous equation set out below. The solution to the equations is simplified using the gas sensitivity identified on each of the sensors and the results reduced to a look-up table accessible by the main controller 25 either on board or on a cloud server.

Equally, the factors correcting for the concentration of ethylene are reduced to data on a lookup table and accessible to the main controller on board or on a cloud server accessible by a wireless module.

$$E_{sens} = E_{true} + \frac{8}{100}M_{true} \quad \quad 1$$

$$M_{sens} = \frac{50}{100}E_{true} + M_{true} \quad \quad 2$$

From 2: $M_{true} = M_{sens} - \frac{50}{100}E_{true}$

Sub into 1:

$$E_{sens} = E_{true} + \frac{8}{100}\left(M_{sens} - \frac{50}{100}E_{true}\right)$$

$$= E_{true} + \frac{8}{100}M_{sens} - \frac{1}{25}E_{true}$$

$$= \frac{24}{25}E_{true} + \frac{8}{100}M_{sens}$$

$$\frac{24}{25}E_{true} = E_{sens} - \frac{8}{100}M_{sens}$$

$$E_{true} = \frac{25}{24}E_{sens} - \frac{1}{12}M_{sens}$$

Maintenance

Several processes are useful for longevity and accuracy. Sensor cleaning (occurs every cycle). For each 3 minute of ethylene readings, the gas sensor is flushed with fresh air for 10-30 mins to restore the humidity and stop sensing chemical reactions.

Removal of water from dehumidification. The conditioner coil will retain ice after a while. This can be removed by heating the coil so the water evaporates or drips out.

Alerts/Alarms

Figure 16:
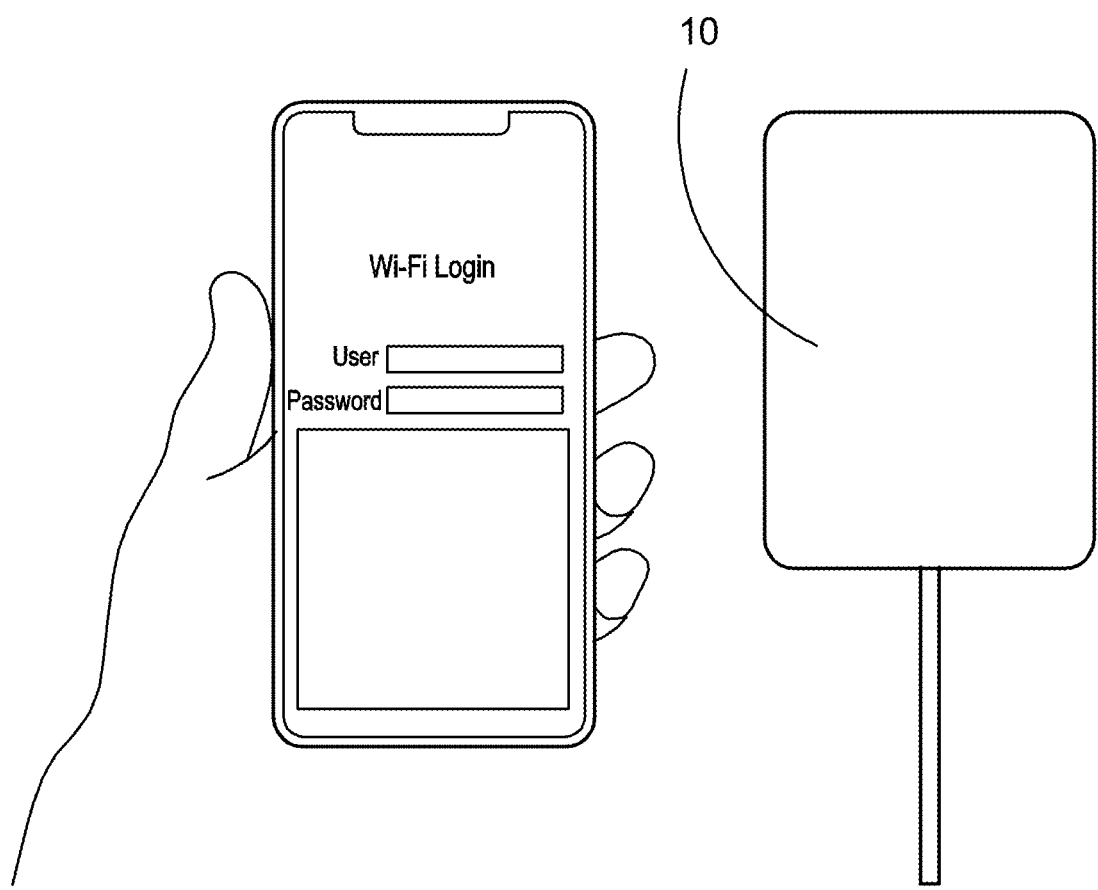
FIG. 16 is an elevation view of a mobile phone showing a login screen and a device of an embodiment of the present invention inside a housing in the background.

As indicated by FIG. 16 there may be an assessment step in which the main controller 25 compares the amount or concentration of the target gas to a threshold level or rate of increase. Then, the main controller 25 causes the actuation of an alarm sent by SMS or push notification or email by wireless module to a mobile device or computer. The alarm may display on a display or loudspeaker and amplifier on a mobile device or computer.

The alarm step is taken by the processor 25 if the threshold level or rate of increase is exceeded. This allows the wireless module on the main controller 25 to alert users of ethylene concentrations and therefore impending ripeness. This allows users to get fruit to market in a decent state.

Clarifications

Modifications and improvements to the invention will be readily apparent to those skilled in the art. Such modifications and improvements are intended to be within the scope of this invention.

What is claimed:

1. A method of measuring the concentration of a target gaseous or aerosolized compound in a gaseous environment, the method including the steps of:
   extracting a selected sample quantity of the gaseous environment into a target gas measurement system;
   separating the target gaseous or aerosolized compound from the quantity of sample gas, into a store;
   sensing, with a target gas sensor, the amount or concentration of the target gaseous or aerosolized compound from the store,
   sensing with a gas sensor, at least one second gas component selected from the group consisting of: oxygen, carbon dioxide, carbon monoxide, and volatile organic compounds;
   receiving in a processor, data from the target gas sensor relating to the amount or concentration of the target gaseous or aerosolized compound;
   converting, in the processor, the target gas sensor data, with a conversion algorithm, to obtain environmental concentration data of the target gaseous or aerosolized compound by adjusting the concentration data with reference to a target sensor sensitivity to the at least one second gas component; and
   storing in a data store or displaying on a display, the environmental concentration data, or transmitting the environmental concentration data to a remote server or processor.

2. The method in accordance with claim 1 further including the step of measuring with a sample gas sensor the quantity of the gas sample in the gas measurement system.

3. The method in accordance with claim 1 including the step of receiving, into the processor, data relating to the selected quantity of sample gas.

4. The method in accordance with claim 1 wherein the algorithm takes into account data from a sample gas sensor relating to a sample gas quantity and/or one or more physical qualities taken from the group consisting of: temperature, volume, pressure, and humidity.

5. The method in accordance with claim 1, further comprising calculating, in the processor, a baseline-adjusted amount or concentration of the target gaseous or aerosolized compound by subtracting a baseline target gas amount from a peak target gas amount in the store, wherein the baseline corresponds to the gaseous environment.

6. The method in accordance with claim 1 wherein the amount or concentration of the target gaseous or aerosolized compound is calculated by measuring an area under a concentration data curve over time from release from the store.

7. The method in accordance with claim 1 further including the step of extracting the gas from the store to a target gas sensor unit, for sensing the amount of target gaseous or aerosolized compound.

8. The method in accordance with claim 1 further including the step of conditioning the selected sample quantity of gaseous environment to a selected physical state to provide a conditioned gas sample for input to the separation step.

9. The method in accordance with claim 8 wherein the conditioning step includes dehumidifying the gas sample.

10. The method in accordance with claim 1 wherein the separation step is conducted in a concentrator module, in which the store is disposed, to store a storage matrix.

11. The method in accordance with claim 10 wherein the storage matrix is activated carbon.

12. The method in accordance with claim 1 wherein ethylene is the target gaseous or aerosolized compound and the separation step is adsorption of ethylene.

13. The method in accordance with claim 1 wherein the sensing step includes desorption from the store of, and sensing in the target gas sensor of, ethylene.

14. The method in accordance with claim 1 further including an assessment step in which the processor compares the amount or concentration of the target gaseous or aerosolized compound to a threshold level or rate of increase.

15. The method in accordance with claim 14 further including an alarm actuation step in which a wireless module transmits an alarm to a display or loudspeaker and amplifier on a mobile device or computer.

16. The method in accordance with claim 15 wherein the alarm step is taken if the threshold level or rate of increase is exceeded.

17. The method of claim 1, wherein the conversion algorithm comprises applying a linear model to obtain an estimate of the concentration of the target gaseous or aerosolized compound, based on the sensed amount or concentration of the target gaseous or aerosolized compound from the store.

18. A gas component monitor for monitoring the concentration of a target gaseous or aerosolized compound in a gaseous environment, the monitor system including:
- a pump for extracting from an environment a sample of gas of a selected or predetermined quantity from the environment;
- a concentrator module which includes a separator for separation of the target gaseous or aerosolized compound from the gas sample, the separator including a store for storage of a target gaseous or aerosolized compound;
- a target gas component sensor module configured to:
  - sense the concentration or amount of the gaseous or aerosolized compound in the store; and
  - sense at least one second gas component selected from the group consisting of:
- oxygen, carbon dioxide, carbon monoxide, and volatile organic compounds; and
- a processor connected to the target gas component sensor module, the processor configured to calculate the environmental concentration of the target gaseous or aerosolized compound based on a conversion algorithm that adjusts the concentration data with reference to a target sensor sensitivity to the at least one second gas component.

\* \* \* \* \*